United States Patent [19]

Gerosa et al.

[11] Patent Number: 5,724,257
[45] Date of Patent: Mar. 3, 1998

[54] FOUNDRY SAND TESTING APPARATUS AND SYSTEM

[75] Inventors: Ricardo Mario Gerosa; Horacio Marcelo Gerosa. both of Rosario, Argentina; Scott M. Strobl. Aurora, Ill.

[73] Assignee: Simpson Technologies Corporation, Aurora, Ill.

[21] Appl. No.: 635,291

[22] Filed: Apr. 19, 1996

[51] Int. Cl.$^6$ .............................. G01N 3/00; G01N 3/08; G01N 5/02
[52] U.S. Cl. ...................... 364/508; 73/73; 73/794; 73/805; 73/823; 73/833
[58] Field of Search ...................... 364/508, 506; 73/760, 788, 794, 805, 823, 826, 833

[56] References Cited

U.S. PATENT DOCUMENTS

| | | | |
|---|---|---|---|
| Re. 25,475 | 11/1963 | McIlvaine | 241/124 |
| 2,263,797 | 11/1941 | Christensen | 22/89 |
| 2,277,953 | 3/1942 | Christensen | 175/183 |
| 2,978,147 | 4/1961 | McIlvaine | 222/185 |
| 3,638,478 | 2/1972 | Dietert et al. | 73/73 |
| 3,808,881 | 5/1974 | Dietert | 73/794 |
| 3,826,902 | 7/1974 | Claxton et al. | 364/508 |
| 4,073,185 | 2/1978 | Griffin | 73/833 |
| 4,114,420 | 9/1978 | Browning | 374/49 |
| 4,368,984 | 1/1983 | Rikker | 366/15 |
| 4,713,294 | 12/1987 | Armbruster et al. | 428/404 |
| 4,802,367 | 2/1989 | Petersen et al. | 73/805 |
| 4,930,354 | 6/1990 | Knopp et al. | 73/823 |
| 5,226,310 | 7/1993 | Steier | 73/38 |

*Primary Examiner*—Emanuel T. Voeltz
*Assistant Examiner*—Demetra R. Smith
*Attorney, Agent, or Firm*—Mason, Kolehmainen, Rathburn & Wyss

[57] ABSTRACT

Foundry sand testing apparatus, method and system are provided for testing foundry sand. A computer foundry sand testing system includes at least one sensor for sensing predetermined characteristics of the foundry sand and for generating a signal. A processor coupled to the sensor processes the generated signal. A display is operatively controlled by the processor for displaying predetermined test information responsive to the generated signal. Predefined displays for receiving user selections and for displaying of test information are automatically generated. The generated displays of test information include real-time stress-strain curves and multiple calculated values utilizing the stress-strain curves.

23 Claims, 15 Drawing Sheets

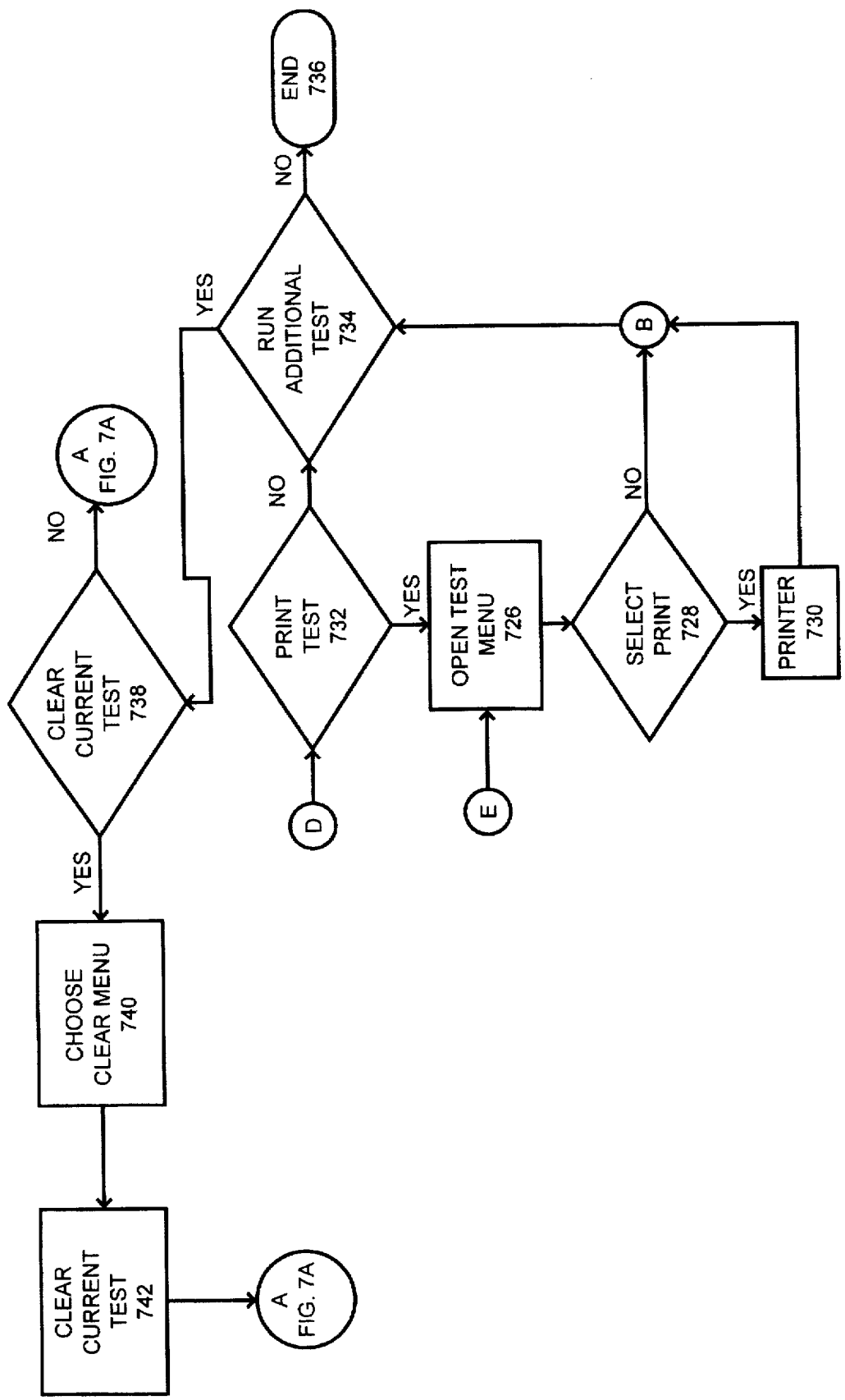

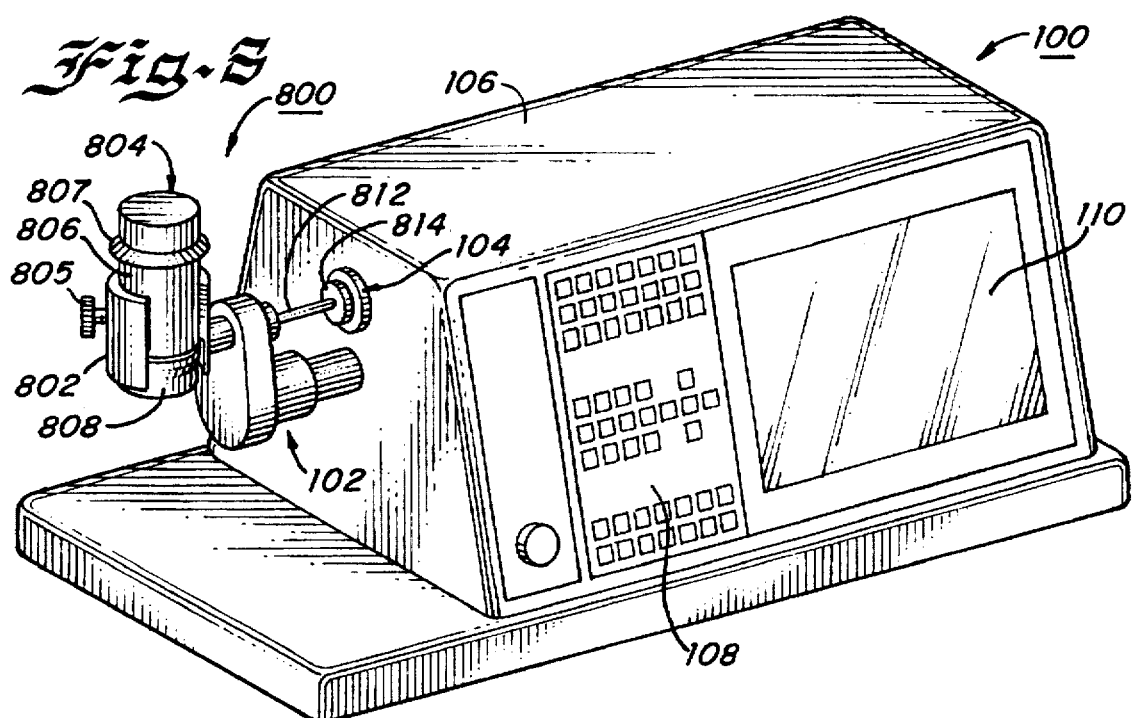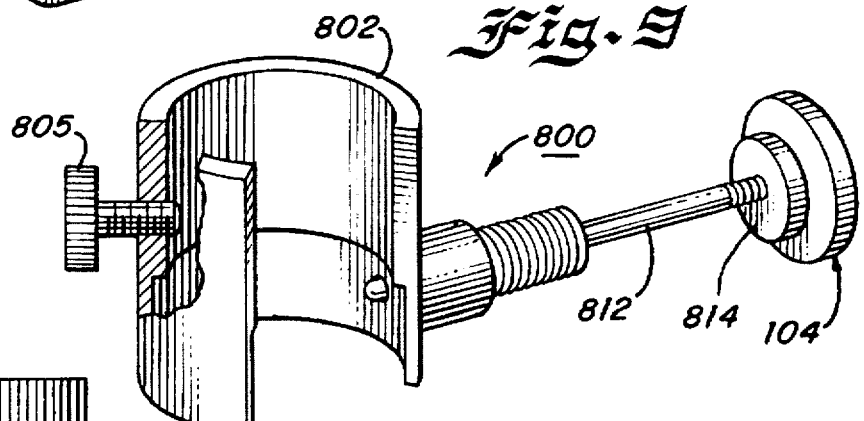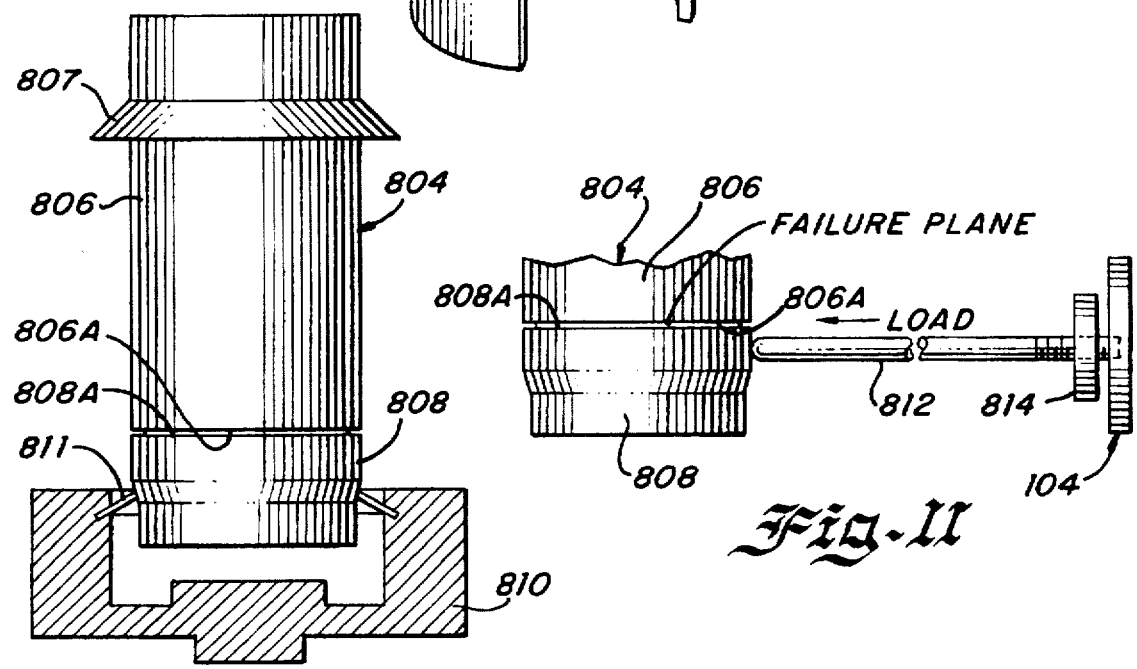

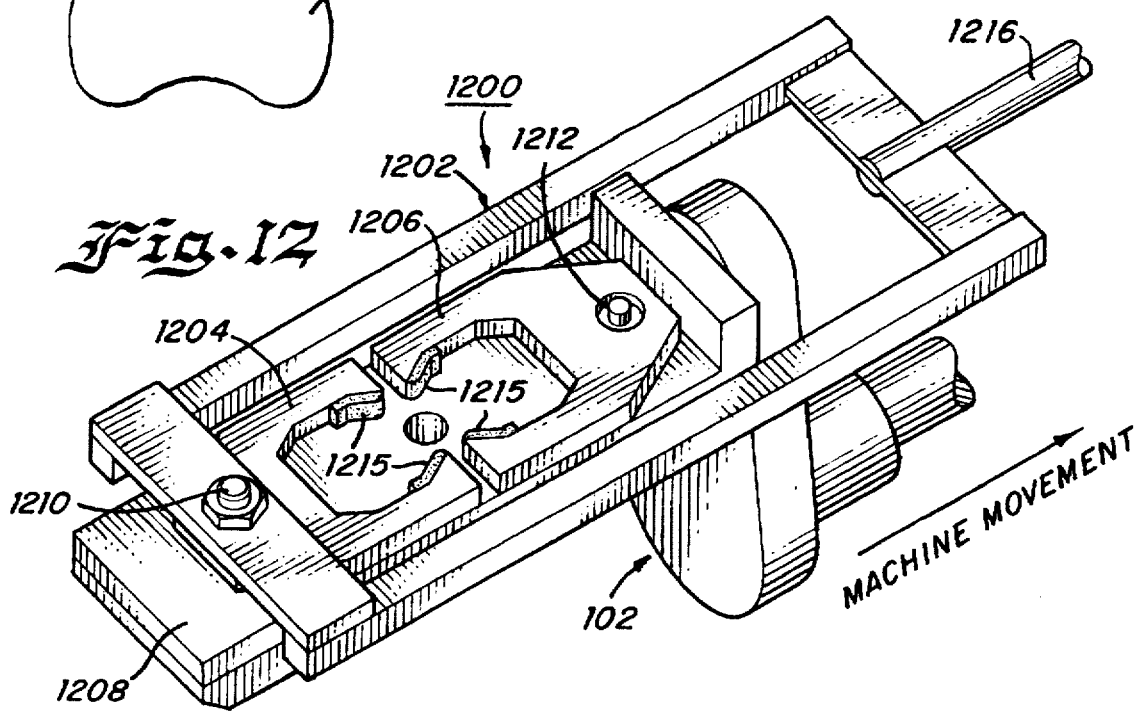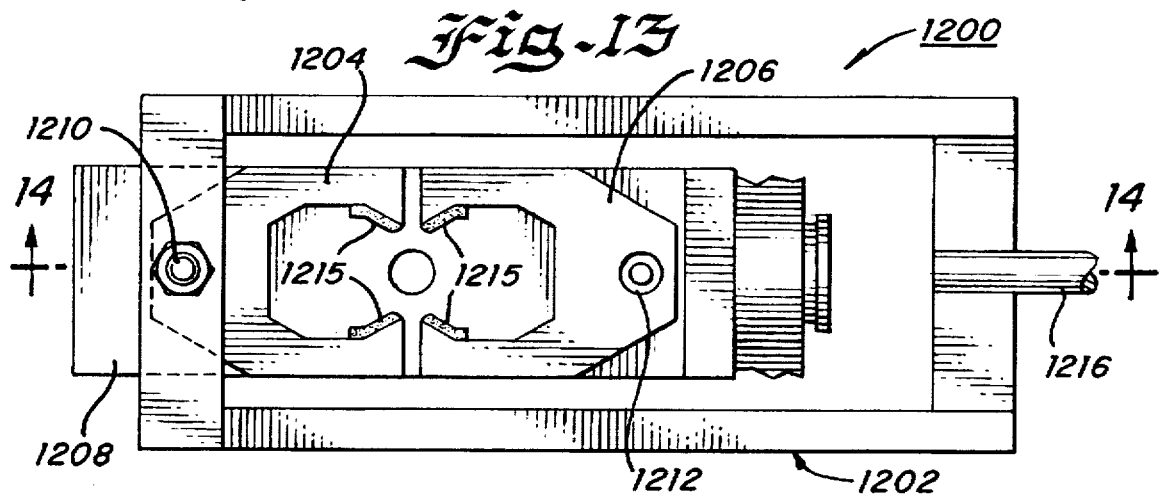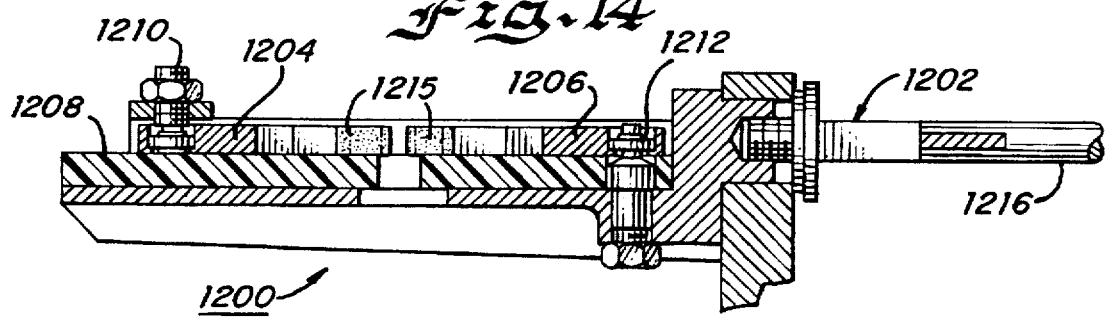

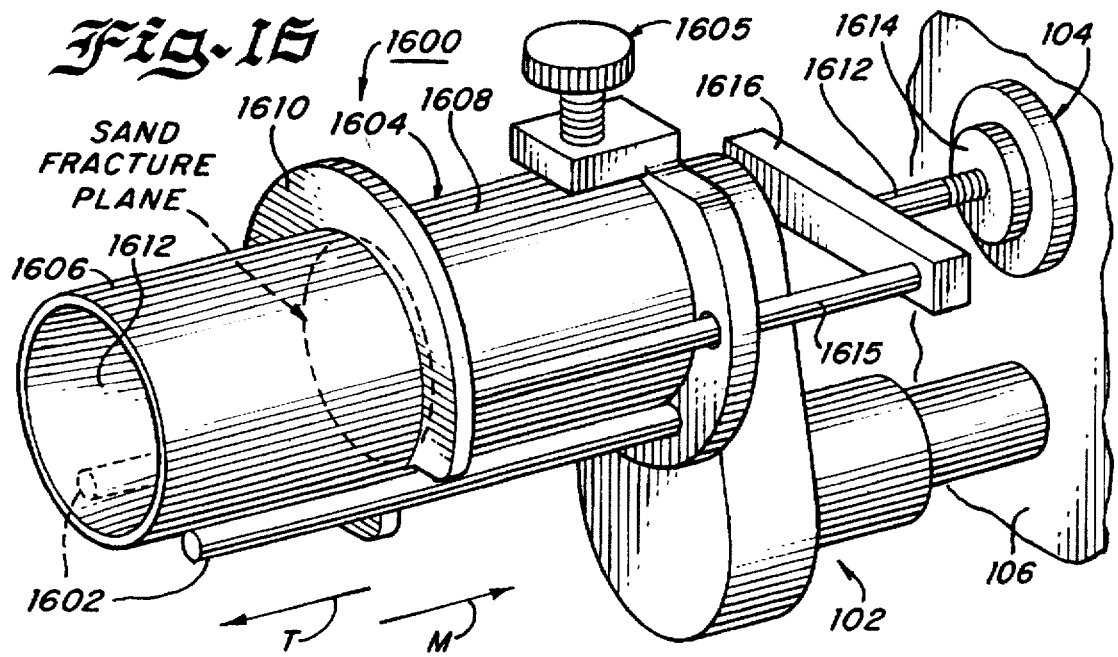
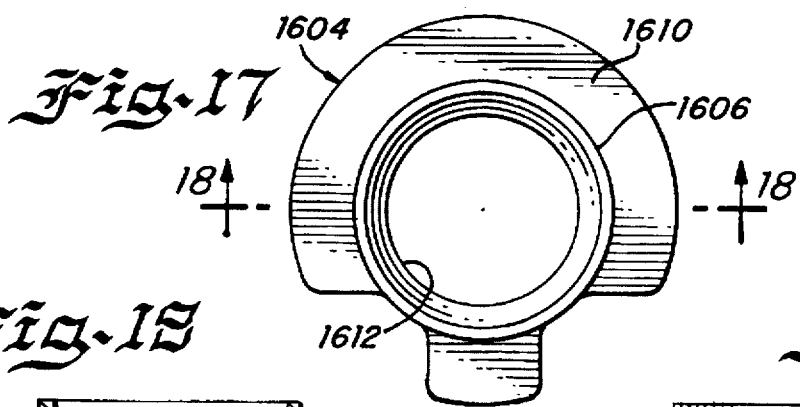
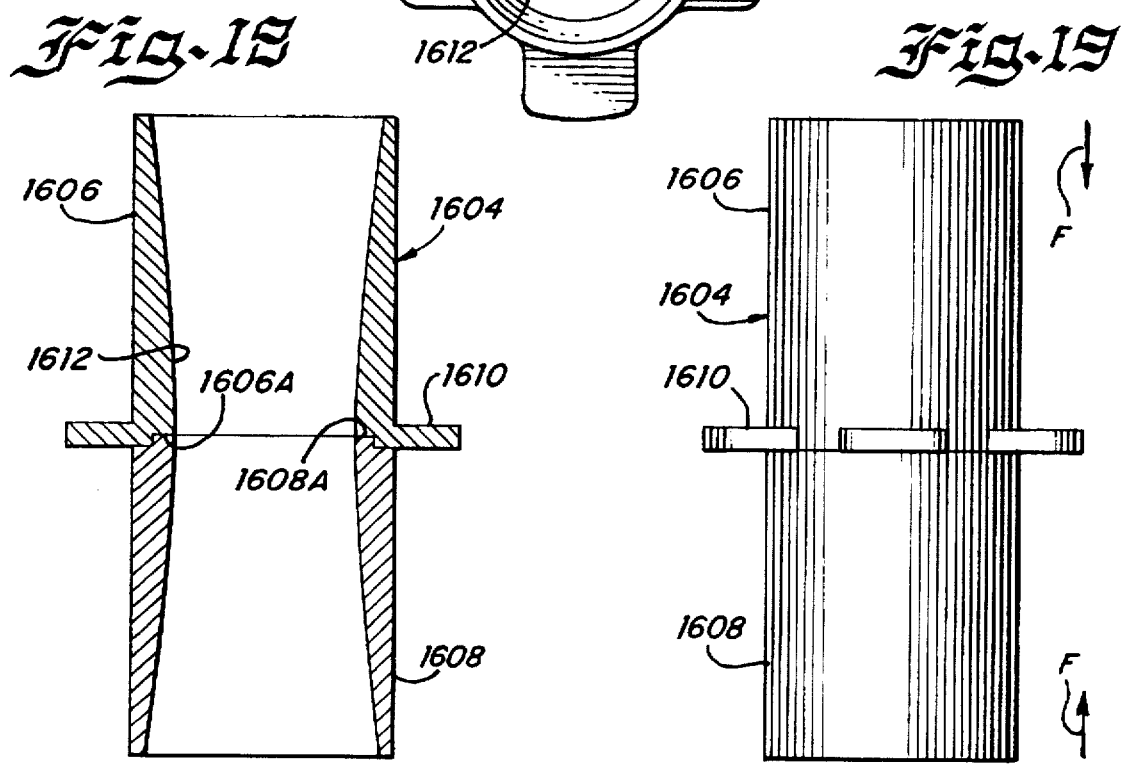

FOUNDRY SAND TESTING APPARATUS AND SYSTEM

FIELD OF THE INVENTION

The present invention relates to computerized foundry sand testing methods, apparatus and system.

DESCRIPTION OF THE PRIOR ART

Known arrangements for testing of foundry sand do not effectively identify many important characteristics of the foundry sand. Known foundry sand testing arrangements while typically complex, provide limited information to facilitate proper conditioning or reconditioning for effective use of the foundry sand being tested. As used in the following description and claims, it should be understood that foundry sand includes bentonite or clay bonded sand, often referred to as green sand, and chemically bonded sand. As used in the following description and claims, the terms stress and strength are used interchangeably and similarly, the terms strain and deformation are used interchangeably.

A need exists for improved methods for testing foundry sand, improved foundry sand testing apparatus and system for testing foundry sand. It is desirable to provide improved apparatus for clay bonded sand or green sand tensile testing. It is desirable to provide improved green sand compression testing apparatus. It is desirable to provide improved green sand shear deformation testing apparatus. It is desirable to provide improved foundry sand cold shell tensile testing apparatus.

SUMMARY OF THE INVENTION

A principal object of the present invention is to provide improved methods for testing foundry sand, improved foundry sand testing apparatus and system for testing foundry sand. Other important objects of the present invention are to provide a method and system for testing foundry sand providing stress strain test curves, to provide such method and system that automatically generates and electronically displays predetermined test information; to provide such method and system that solves problems of performance and cost; to provide such method and system that overcomes many of the disadvantages of prior art arrangements.

In brief, foundry sand testing apparatus, method and system are provided for testing foundry sand. A computer foundry sand testing system includes at least one sensor for sensing predetermined characteristics of the foundry sand and for generating a signal. A processor coupled to the sensor processes the generated signal. A display is operatively controlled by the processor for displaying predetermined test information responsive to the generated signal.

Predefined displays for receiving user selections and for displaying test information are automatically generated. The generated displays of test information include real-time stress-strain curves and multiple calculated values utilizing the stress-strain curves.

BRIEF DESCRIPTION OF THE DRAWINGS

The present invention together with the above and other objects and advantages may best be understood from the following detailed description of the preferred embodiments of the invention illustrated in the drawings, wherein:

FIGS. 7A 7B and 7C together provide a flow chart illustrating a test data processing and displaying method for foundry sand testing in accordance with the invention;

FIG. 8 is a perspective view illustrating a shear deformation testing accessory together with a shear deformation specimen tube and the foundry sand testing computer system of FIG. 1 in accordance with the invention;

FIG. 9 is a perspective view illustrating the shear deformation testing accessory of FIG. 8;

FIG. 10 is a plan view illustrating the a shear deformation specimen tube of FIG. 8;

FIG. 11 is a fragmentary side elevational view illustrating operation of the shear deformation testing accessory of FIG. 8;

FIG. 12 is a perspective view illustrating a cold shell tensile testing accessory for the foundry sand testing computer system of FIG. 1 in accordance with the invention;

FIG. 13 is a top plan view of the cold shell tensile testing accessory of FIG. 12;

FIG. 14 is a sectional view of the cold shell tensile testing accessory taken along line 13—13 of FIG. 13;

FIG. 15 is an enlarged plan view illustrating a specimen used with the cold shell tensile testing accessory of FIG. 12;

FIG. 16 is a perspective view illustrating a green sand tensile testing accessory for the foundry sand testing computer system of FIG. 1 in accordance with the invention;

FIG. 17 is an end plan view illustrating a green sand tensile testing specimen tube of the illustrating a green sand tensile testing accessory of FIG. 16;

FIG. 18 is a sectional view of the green sand tensile testing specimen tube taken along line 18—18 of FIG. 17; and FIG. 19 is a side plan view of the green sand tensile testing specimen tube of FIG. 16 illustrating preparation of the green sand sample to be tested in the specimen tube in accordance with the invention.

DETAILED DESCRIPTION OF THE PREFERRED EMBODIMENTS

In accordance with the present invention, foundry sand testing methods and a computer foundry sand testing system are provided which automatically generates predefined displays for receiving user selections and automatically generates displays of test information for the foundry sand specimens or samples being tested. The generated displays of test information include real-time stress-strain curves for a sample being tested and multiple calculated values utilizing the stress-strain curves.

Figure 1:
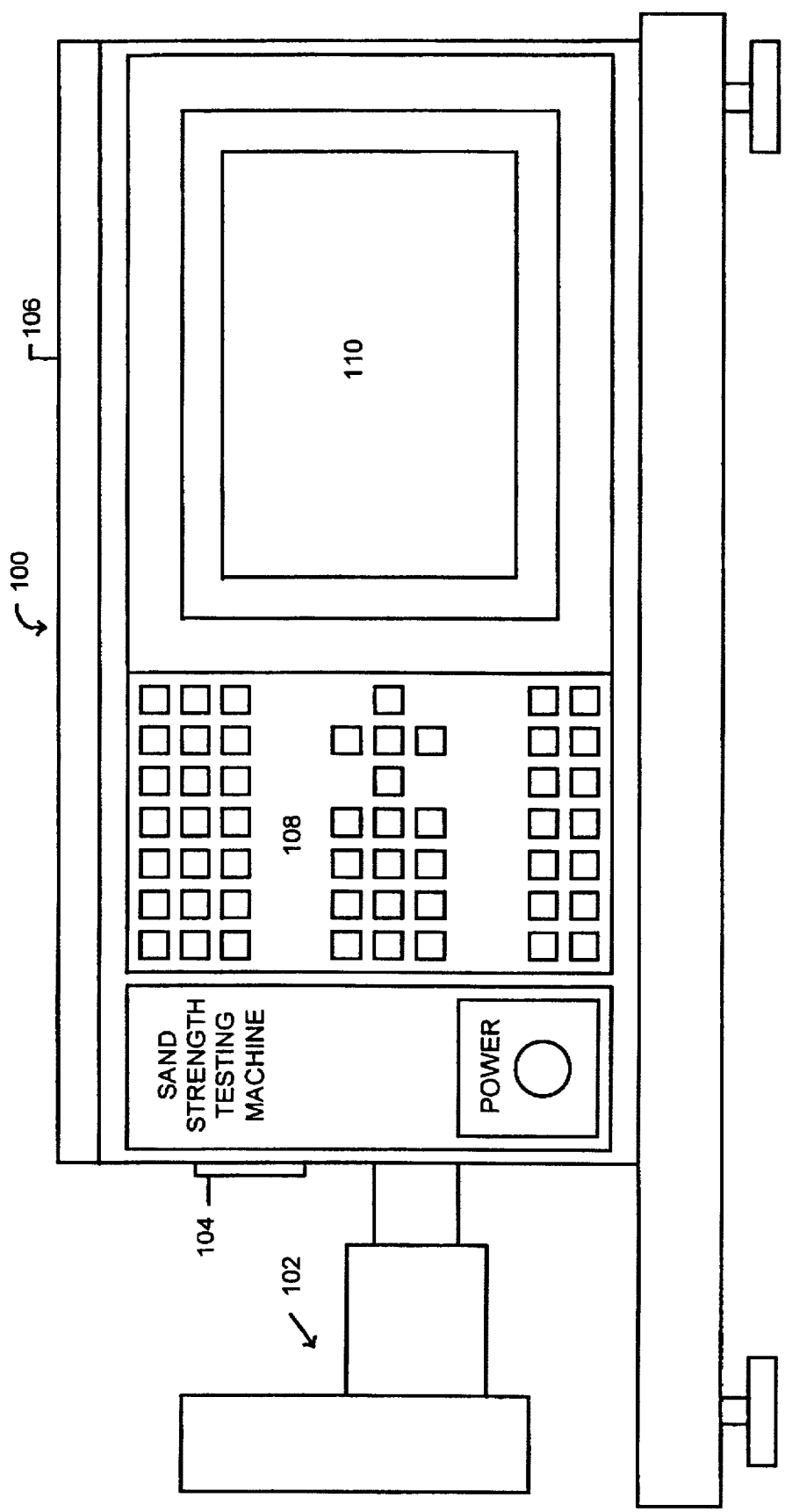
FIG. 1 is a schematic and block diagram representation illustrating a computer system for testing foundry sand in accordance with the invention.
Figure 2:
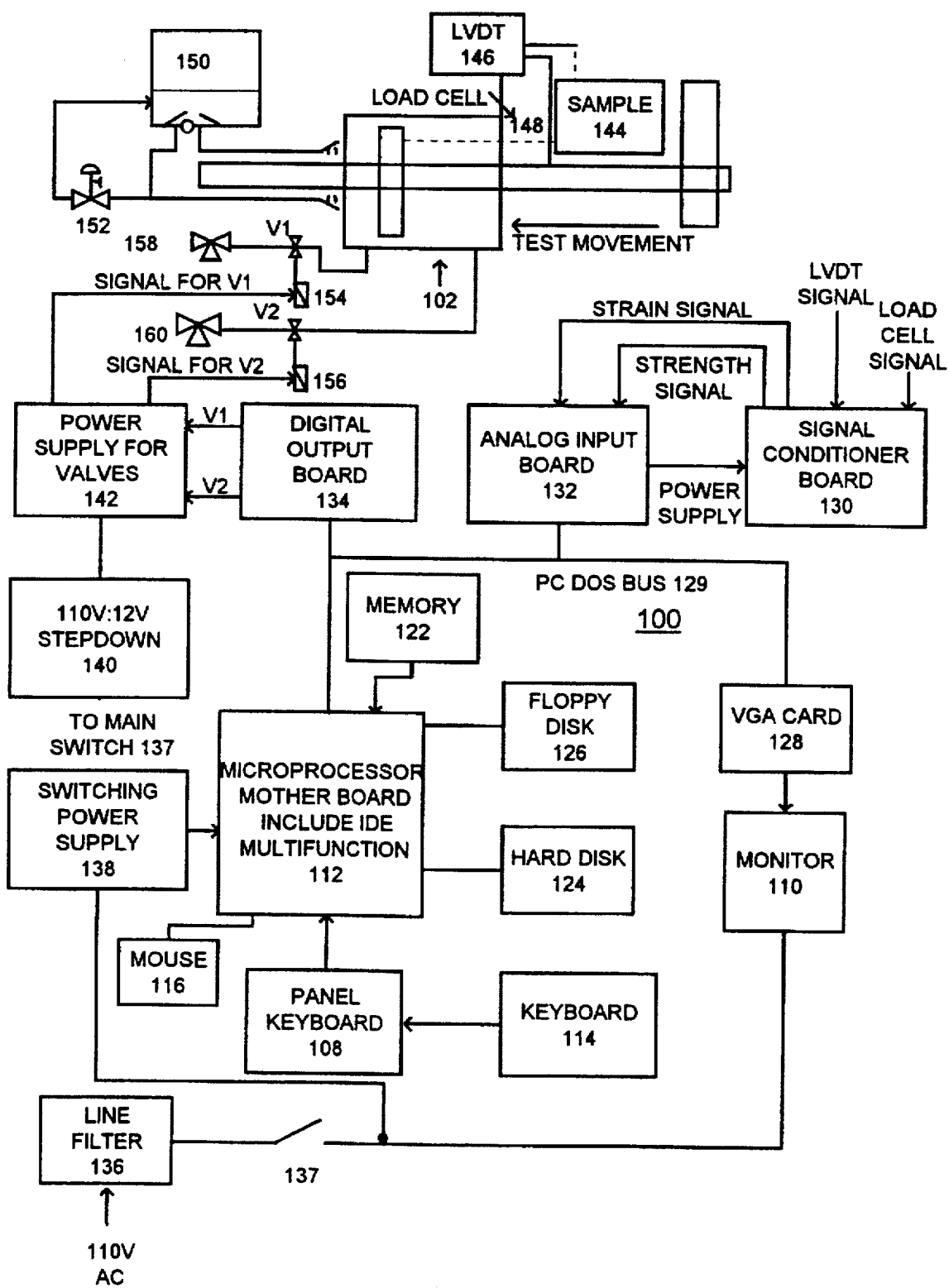
FIG. 2 is a more detailed schematic and block diagram illustrating the foundry sand testing computer system of FIG. 1 in accordance with the invention.

Having reference now to the drawings, in FIGS. 1 and 2, there is shown a computer system for testing foundry sand generally designated by 100 and arranged in accordance with the invention. Computer foundry sand testing system 100 includes a moveable arm 102 and a jaw support 104 carried by a housing 106 for receiving a plurality of conventional testing accessories or strength testing attachments.

Moveable arm 102 and the jaw support 104 also receive novel testing accessories including a shear deformation testing accessory 800 illustrated and described with respect to FIGS. 8–11, a cold shell tensile testing accessory 1200 illustrated and described with respect to FIGS. 12–15 and a green sand tensile testing accessory 1600 illustrated and described with respect to FIGS. 16–19 of the invention. Computer foundry sand testing system 100 includes a keyboard panel 108 for receiving user selections, a display or monitor 110 for displaying multiple predefined menus, operational parameters and test results of the invention.

Having reference to FIG. 2, computer foundry sand testing system 100 includes a microprocessor mother board including IDE multifunction 112 or microprocessor 112 suitably programmed for performing the foundry sand testing methods of the invention, as illustrated and described with respect to FIGS. 5A, 5B, 6, 7A and 7B. Computer foundry sand testing system 100 optionally includes an keyboard 114 and a mouse 116 for receiving user or operator input selections. Computer foundry sand testing system 100 includes a memory 122, such as a dynamic random access memory, coupled to the microprocessor 112 for storing program and testing and parameter data. Computer foundry sand testing system 100 includes a hard disk memory 124 and a floppy disk memory 126.

Computer foundry sand testing system 100 includes a VGA card 128 driving the display 110 that is coupled to the microprocessor 112 by an internal PC DOS bus 129. Computer foundry sand testing system 100 includes a signal conditioner board 130 for receiving a strength representative signal and a strain representative signal of a foundry sand sample being tested as indicated at a respective line labelled LOAD CELL SIGNAL and LVDT SIGNAL. A STRAIN SIGNAL and a STRESS SIGNAL are applied to an analog input board 132 coupled to the signal conditioner board 130. Computer foundry sand testing system 100 includes a digital output board 134 providing testing control signals at lines labelled V1 an V2. The internal PC DOS bus 129 facilitates communications among the components of 100. Computer foundry sand testing system 100 includes a power line filter 136 coupled between an AC power supply, such as 110V AC line and a main switch 137. A switching power supply 138 provides a low voltage power supply input to the microprocessor 112 and the signal conditioner board 130, as indicated at a line labelled POWER SUPPLY.

Computer foundry sand testing system 100 includes a STEPDOWN power transformer 140 coupled to the main switch 136 and a power supply 142. Power supply 142 receives the control signals V1 and V2 and provides valve control signals at lines SIGNAL FOR V1, SIGNAL FOR V2 for a pair of solenoid valves (V1 and V2) 154 and 156 operatively controlled for moving the moveable arm 102 to both start and stop a particular test. A sample of foundry sand sample 144 to be tested is loaded within a particular testing accessory carried by moveable arm 102. A direction of movement of arm 102 is indicated by an arrow labelled MOVEMENT in FIG. 2. Computer foundry sand testing system 100 includes a linear variable displacement transducer (LVDT) 146 and a load cell 148. The LVDT 146 generates a strain representative signal and load cell 148 generates a stress representative signal of the foundry sand sample 144 being tested. Computer foundry sand testing system 100 includes an oil reservoir 150 providing a hydraulic brake to the moveable arm 102 to avoid changes in generated stress-strain curves that otherwise could result with compressed air. A control valve 152 is coupled to the oil reservoir 150 and moveable arm 102. A flow control valve 158 is connected to the solenoid valve V1, 154 and a flow control valve 160 is connected to the solenoid valve V2, 156.

Figure 3:
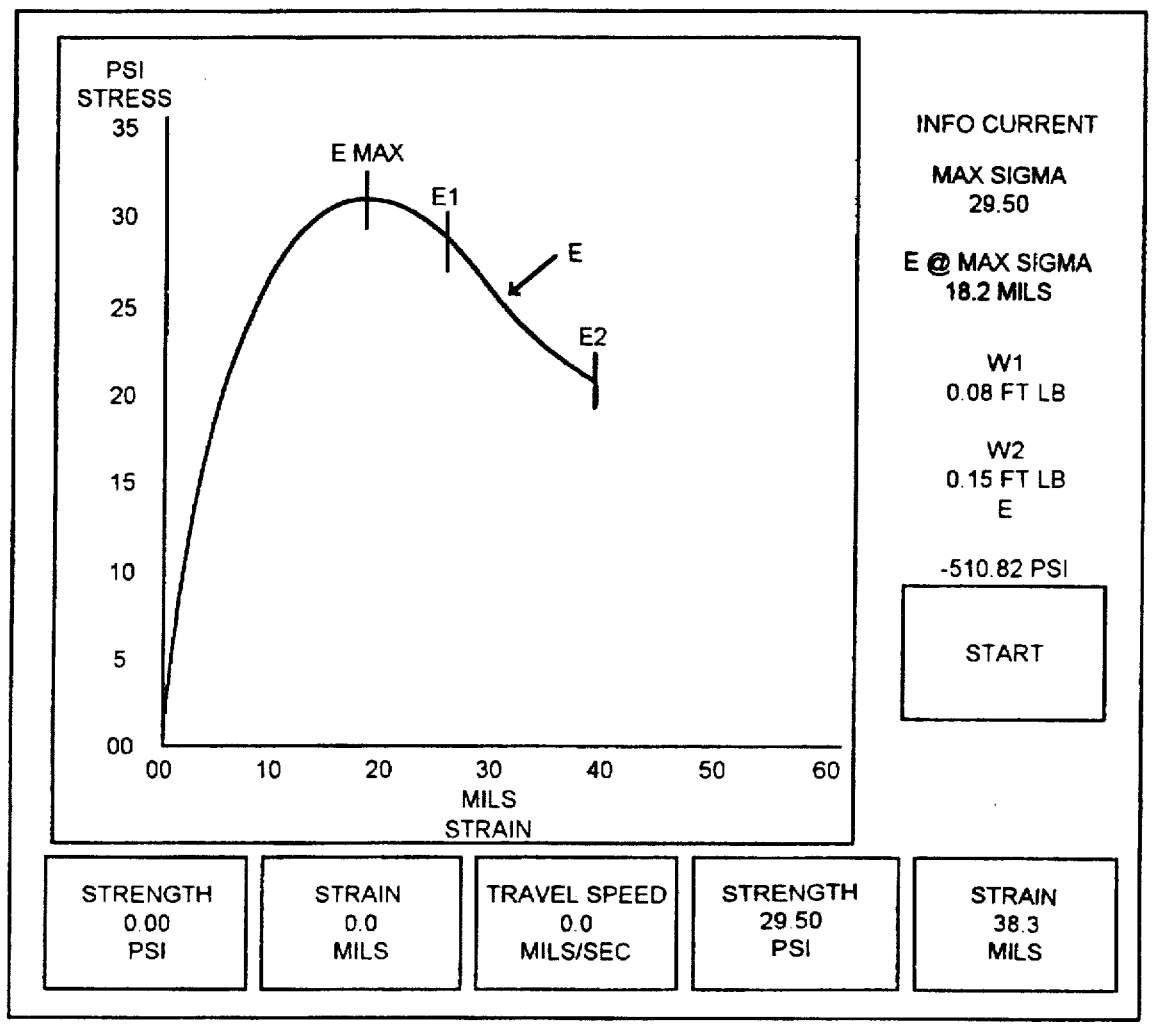
FIGS. 3 and 4 are diagrams illustrating exemplary testing displays generated by the foundry sand testing computer system of FIG. 1 in accordance with the invention.
Figure 4:
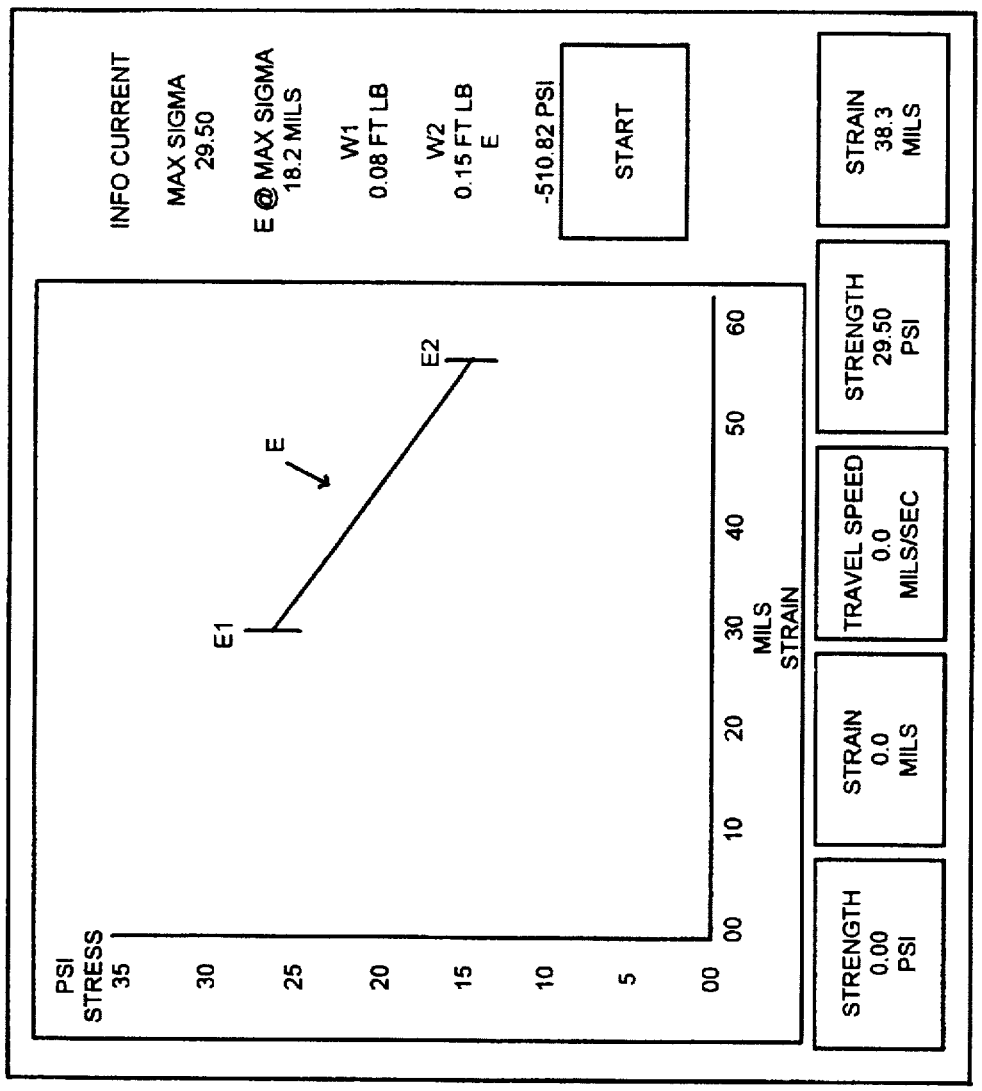

FIGS. 3 and 4 illustrate exemplary testing displays generated by the foundry sand testing computer system 100 in accordance with the invention. Referring initially to FIG. 3, an illustrated green sand compression stress-strain curve is generated together with strength, strain, and travel speed values in real-time with testing of a foundry sand sample 144. A maximum stress value, represented by MAX SIGMA, is identified and displayed. A first area from 0 stress to MAX SIGMA under the stress-strain curve, W1 is calculated and displayed as a numerical value below W1 of Ft Lbs or Joules depending on a user selection of American Foundrymen's Society (AFS) or metric for the particular test. A second area from MAX SIGMA to E2 under the stress-strain curve, W2 is calculated and displayed. The E2 value is a user selected cutoff value following the MAX SIGMA value, such as a selected percentage of MAX SIGMA, for example, between 50% to 75% of MAX SIGMA. A falling slope of a line shown in FIG. 4 from another user selected value E1 to E2 is calculated and displayed below the W2 calculated value. The calculated falling slope is represented by E. The user selected value E1 can be another selected percentage of MAX SIGMA, for example, between 80% to 85% of MAX SIGMA.

Figure 5A:
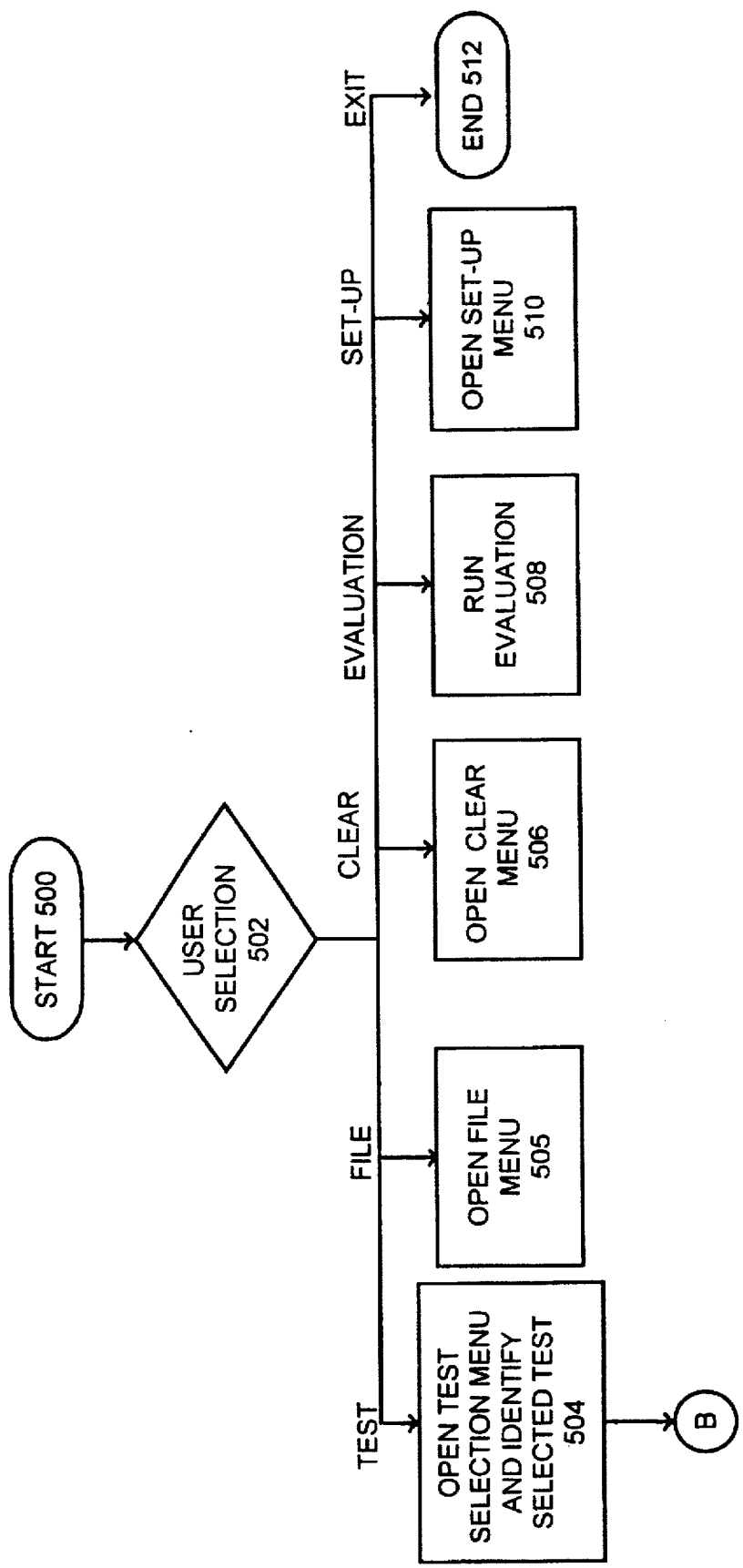
FIGS. 5A and 5B together provide a flow chart illustrating a main process for foundry sand testing in accordance with the invention.
Figure 5B:
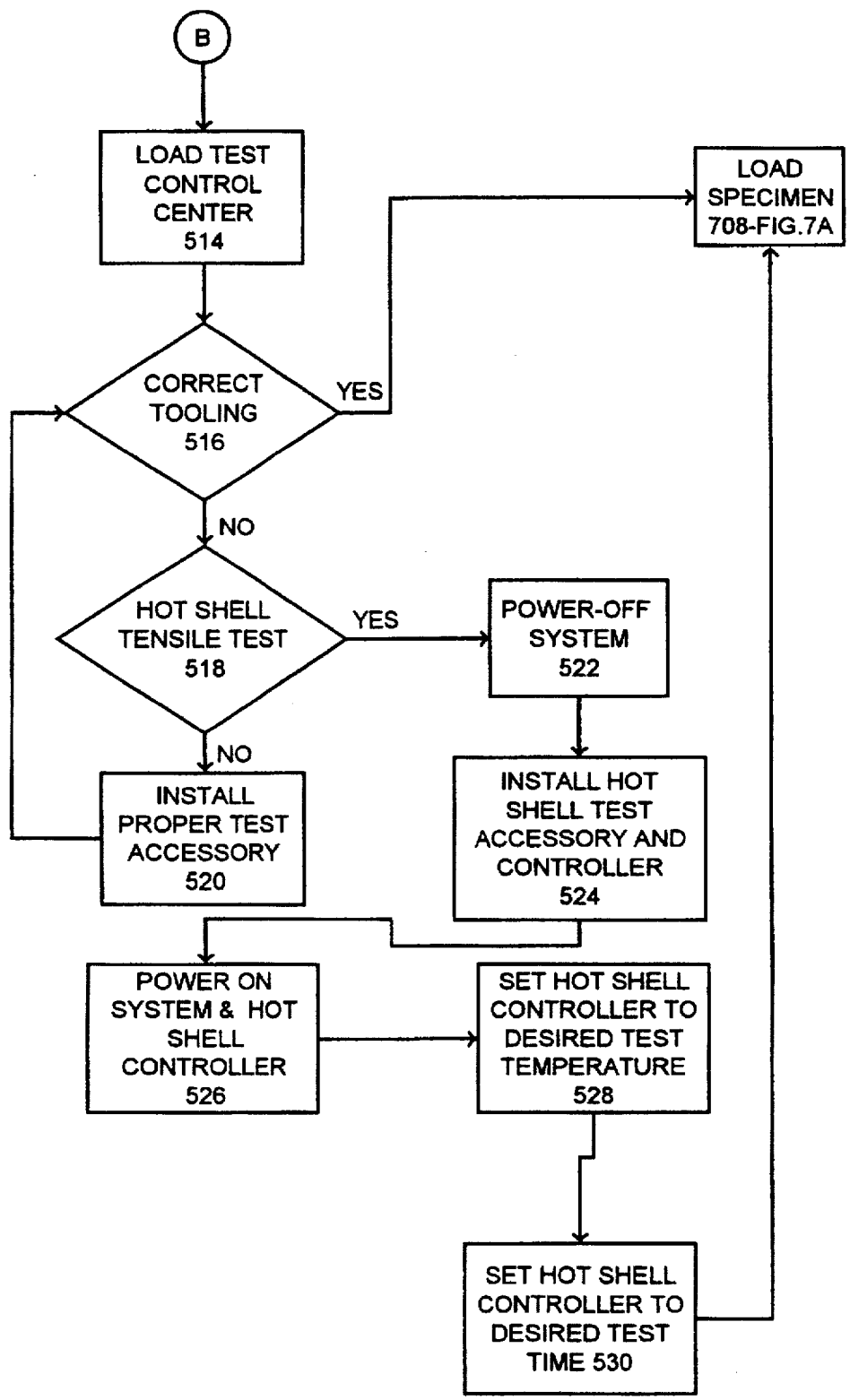

Referring now to FIGS. 5A and 5B, there is shown a flow chart illustrating a main process for foundry sand testing in accordance with the invention. The sequential steps starting at a block 500 begin with a user main menu selection as indicated at a block 502 and end at a block 512 with a user exit selection. At block 502, a main screen displays the main menu selections and a current status bar. Computer foundry sand testing system 100 is arranged to be operated in a user friendly windows type environment. Machine set up and operation is made simple through a series of pull down menus and command bars.

Responsive to a user test selection at block 502, a test selection menu is opened and a user selected test is identified as indicated at a block 504. The test selection menu opened at block 504 allows the operator to choose from multiple sand test selections including compressive strength, shear strength, shear deformation, splitting strength, transverse double shear strength, core tensile strength, shell hot and cold tensile strength, green sand tensile strength, core transverse strength, shell transverse strength and hot shell transverse strength. Microprocessor 120 displays the type of strength test the system 100 is ready to perform. This can be changed by the operator with the test selection input at block 502. Then the sequential operations continue following entry point B in FIG. 5B.

Responsive to a user file selection, a file menu is opened as indicated at a block 505. Responsive to a user clear selection, a clear menu is opened as indicated at a block 506. Responsive to a user evaluation selection, an evaluation of currently displayed test data is performed value as indicated at a block to calculate and draw the falling slope line for the calculated E, as illustrated in FIG. 4. At block 508, the evaluation routine generates the falling slope line, calculating E from the currently displayed stress-strain curve. Multiple stress-strain curves can be evaluated and displayed on one screen at block 508 using a data retrieval selection to load past test curves into the active testing screen. Active test can be easily saved onto the hard drive 124, floppy disk 126 or exported via an RS-232 port of board 134. Responsive to a user set-up selection, a set-up menu is opened as indicated at a block 505.

Referring to FIG. 5B, the test sequential steps continue to load a control center for the selected test as indicated at a block 514. For example, a green sand compression strength test control center loaded at block 514 displays the plot area, test information display, maximum indicators, real time meters, current status bar and menu bar. This control screen is the generated operations display for green sand compression testing. When running a compression test computer foundry sand testing system 100 displays a real time stress-strain curve, numerical real time values of strength, strain and arm travel speed and maximum values for both compressive strength and deformation. The generated display also includes an automatic screen zoom feature that brings the curve to a maximum display size after each test. After each test, the test information panel displays predetermined and test data calculated by system 100 including percent compactability, maximum green compression strength, deformation at maximum strength, area under the stress strain curve before maximum strength W1 and after maximum strength W2 and the falling slope E, for example, as shown in FIGS. 3 and 4. Multiple stress strain curves can be displayed for comparison.

At block 514, with the core tensile strength test control center displays the real time tensile strength development, maximum tensile strength, test information display, current status bar and menu bar. The core tensile strength test control center allows the operator to run up to four tensile strength test. Computer foundry sand testing system 100 automatically calculates and displays the average tensile strength.

Checking whether correct tooling is installed is performed as indicated at a decision block 516. If the correct tooling is installed, then the sequential steps continue with loading a test specimen at indicated at a block 708 in FIG. 7A. Otherwise, if the correct tooling is not installed, then checking whether a hot shell tensile test is selected is made as indicated at a decision block 518. If the hot shell tensile test is not selected, then the proper test accessory is installed as indicated at a block 520, the sequential operations return to decision block 516. Otherwise, when the hot shell tensile test is selected, then system 100 is powered-off as indicated at a block 522. Then the hot shell test accessory and hot shell controller is installed as indicated at a block 524. Then system Computer foundry sand testing system 100 is powered-on to reboot the microprocessor 112 and to start-up the hot shell controller as indicated at a block 526. A desired test temperature is set for the hot shell controller as indicated at a block 528. Then a desired test time is set for the hot shell controller as indicated at a block 530. Then the sequential steps continue with loading a test specimen at block 708 in FIG. 7A.

Figure 6A:
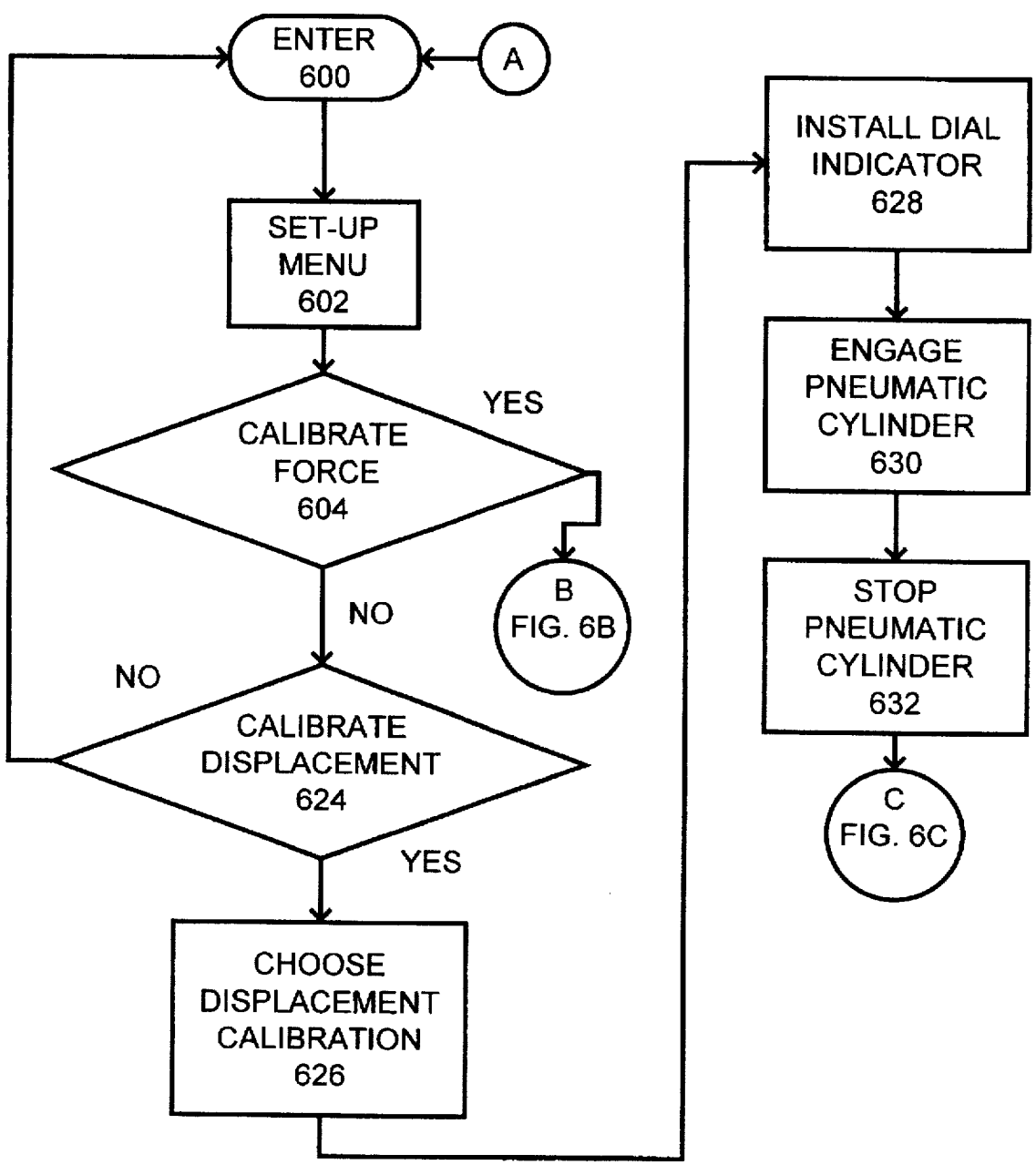
FIGS. 6A, 6B and 6C together provide a flow chart illustrating a calibration process for foundry sand testing in accordance with the invention.
Figure 6B:
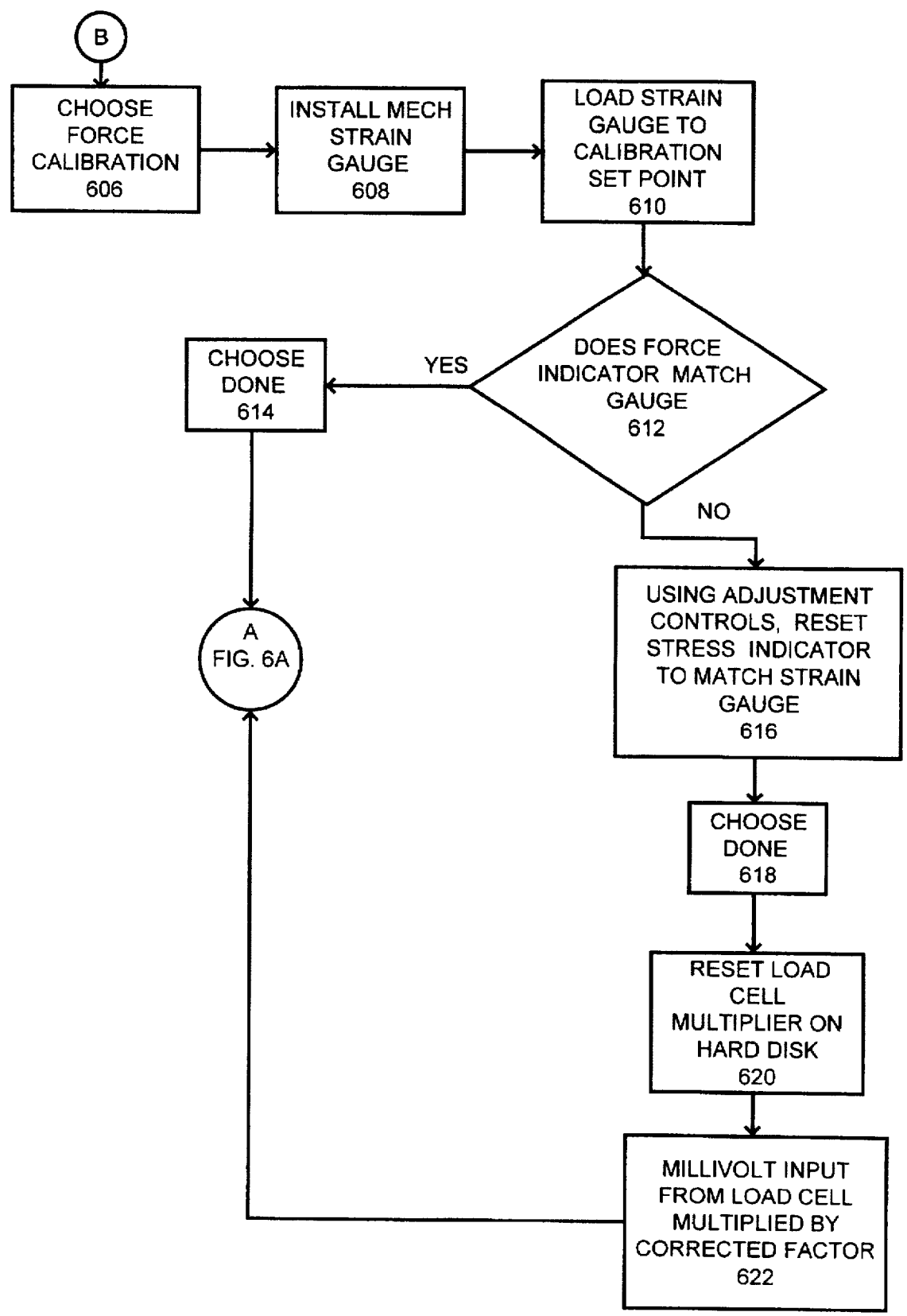
Figure 6C:
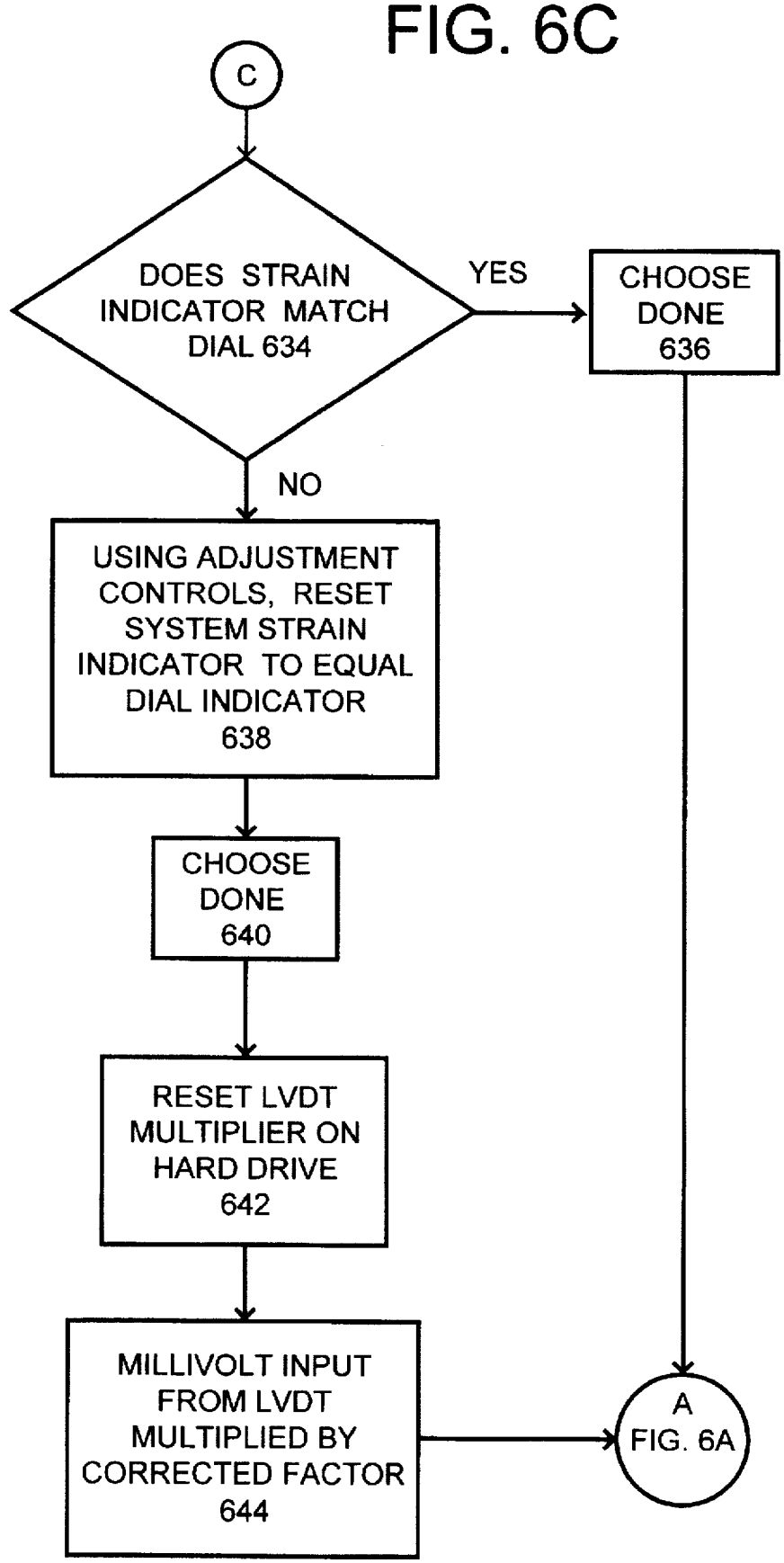

Referring to FIGS. 6A, 6B and 6C, sequential steps of a calibration routine used to digitally calibrate the electronic load cell 148 and the LVDT 146 are shown. This advanced calibration feature of system 100 allows for simple, in shop, calibration. Calibrating the electronic load cell 144 and the LVDT 146 only requires a few minutes from start to finish. If the system 100 is out of calibration, then the operator can make corrections without machine disassembly. The calibration process facilitates self deformation testing by the computer foundry sand testing system 100. This feature allows the system 100 to automatically adjust strain measurements to accommodate the deformation that occurs in the machine components while operating under increasing loads.

The calibration process is entered as indicated at a block 600 in FIG. 6A and begins from a user set-up selection as indicated at a block 602. Checking for a user selection to calibrate force is made as indicated at a decision block 604. If the user has entered the selection to calibrate force, then a force calibration routine is started as indicated at a block 606 in FIG. 6B. A mechanical strain gauge is installed as indicated at a block 608. The mechanical strain gauge is loaded to a particular calibration set point as indicated at a block 610. Then the force indicator of the computer foundry sand testing system 100 is compared with the mechanical strain gauge as indicated at a block 612. If the indicator matches the strain gauge, then done is chosen as indicated at a block 614. Otherwise, using the adjustment controls, the operator reset the strain indicator to equal the set-point or match the strain gauge as indicated at a block 616. Then the load cell multiplier stored on the hard disk 124 is reset as indicated at a block 620. The millivolt input from the load cell is multiplied by the corrected factor as indicated at a block 622. The force calibration routine is completed and the sequential operations return to block 600 in FIG. 6A.

Otherwise, when the user has not entered the selection to calibrate force, checking for a user selection to calibrate displacement is made as indicated at a block 624 in FIG. 6A. If not, and the sequential operations return to block 600. When the user selection to calibrate displacement is identified at block 624, then a displacement calibration routine is started as indicated at a block 626. A dial indicator is installed as indicated at a block 628. A pneumatic cylinder is engaged as indicated at a block 630 and then stopped as indicated at a block 632. Then the strain indicator on computer foundry sand testing system 100 is compared with the dial indicator as indicated at a decision block 634 in FIG. 6C. If the indicators match, then done is chosen as indicated at a block 636 and the sequential operations return to block 600 in FIG. 6A. Otherwise, when the indicators do not match, then the operator uses adjustment controls to reset the system strain indicator to match the dial indicator as indicated at a block 638. Then done is chosen as indicated at a block 640. Then the LVDT multiplier stored on the hard disk 124 is reset as indicated at a block 642. The millivolt input from the LVDT is multiplied by the corrected factor as indicated at a block 644. The displacement calibration routine is completed and the sequential operations return to block 600 in FIG. 6A.

Figure 7A:
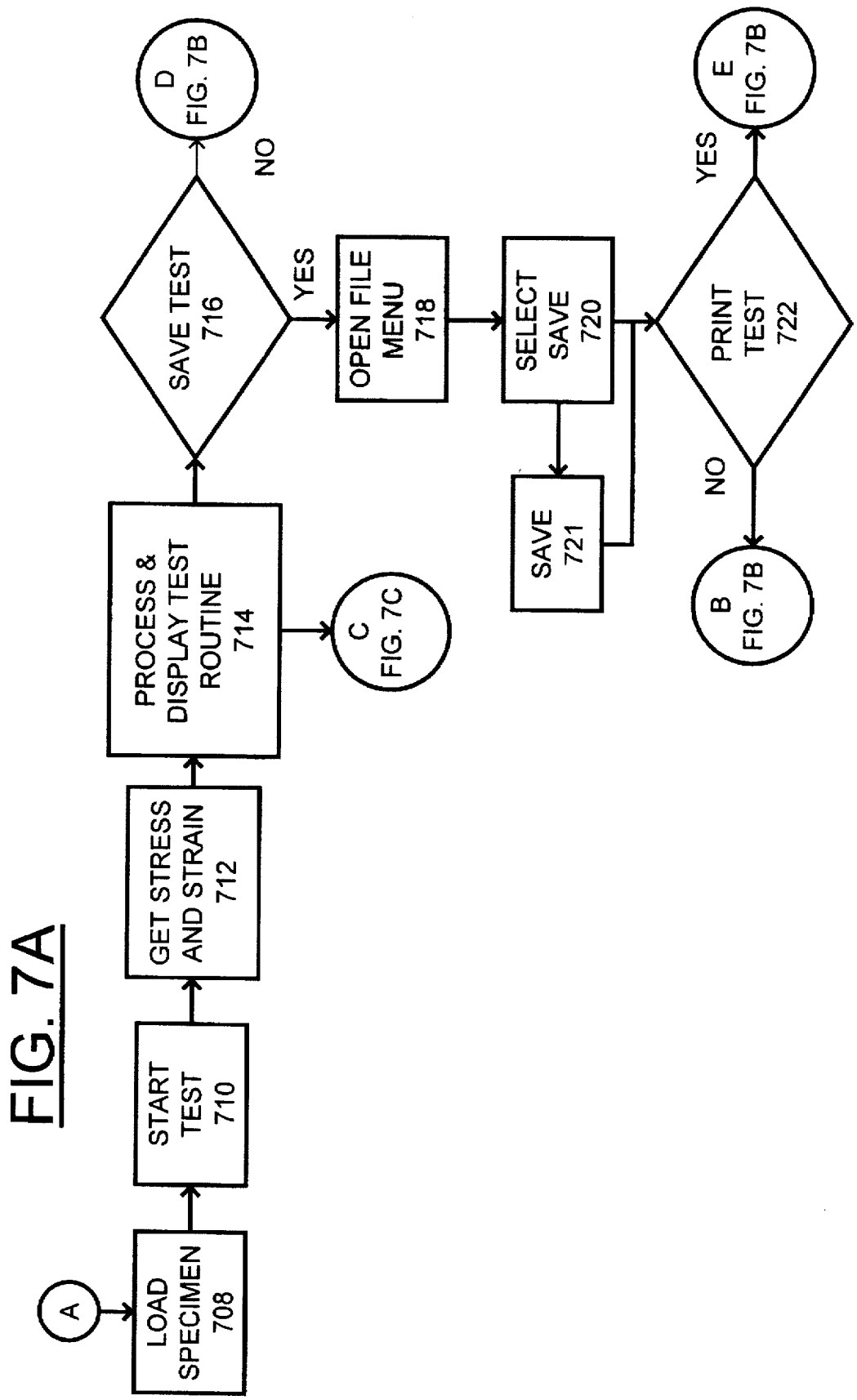
Figure 7C:
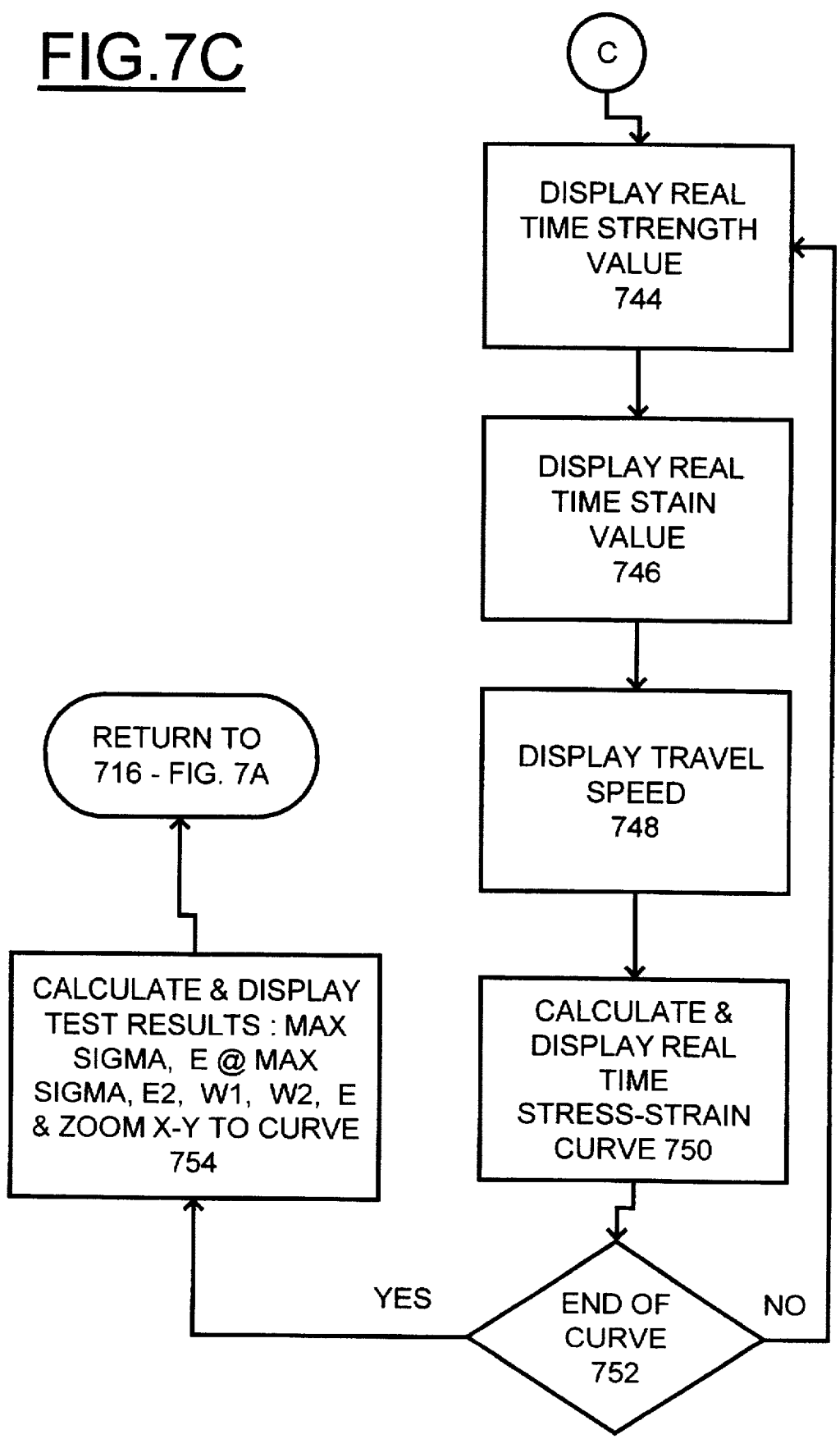

Referring to FIGS. 7A 7B and 7C, the test specimen 144 for the selected test is loaded as indicated at a block 708 in FIG. 7A. An automatic preload adjustment at block 708 allows for easily changed and always constant specimen preloading. The particular selected test is started as indicated at a block 710. A process and display test routine for the particular selected test is run as indicated at a block 714, as illustrated and described with respect to FIG. 7C. Checking for a user selection to save the test is provided as indicated at a decision block 716. If saving is selected by the user, the file menu is opened as indicated at a block 718 and save selected as indicated at a block 720. The current test data is saved as indicated at a block 721. Checking for a user selection to print the test is provided as indicated at a decision block 722. If saving is selected by the user, the file menu is opened as indicated at a block 726 in FIG. 7B and print is selected as indicated at a block 728. The current test data is printed as indicated at a block 730 in FIG. 7B. Otherwise, when save is not selected at block 716 in FIG. 7A, checking for a user selection to print the test is provided as indicated at a decision block 732 in FIG. 7B. If printing is selected by the user, the file menu is opened at block 726.

If printing is not selected by the user at block 732, then checking for a user selection to run an additional test is made as indicated at a block 734 in FIG. 7B. If an additional test has not been selected, then the test sequence ends as indicated at a block 736. Otherwise when an additional test has been selected, then checking for a user selection to clear current test is provided as indicated at a block 738. If true, then the clear menu is chosen as indicated at a block 740 and the current test is cleared as indicated at a block 742 in FIG. 7B. Then the sequential steps continue at block 708 in FIG. 7A with loading a specimen. When the user has not selected to clear the current test, then the sequential steps continue at block 708 with loading a specimen.

Referring now to FIG. 7C, process and display test routine for the particular selected test begins with displaying real time test data including strength as indicated at a block 744, strain as indicated at a block 746 and travel speed of the arm 102 as indicated at a block 748. The real time stress-strain curve for the test is calculated and displayed as indicated at a block 750. These steps are repeated until a user selected E2 value at the end of the stress-strain curve is identified as indicated at a block 752. Then test results are calculated and displayed and zoom the X and Y axis to fit the stress-strain curve as indicated at a block 754. Then the sequential steps return to block 716 in FIG. 7A with checking for a user save test selection.

Referring to FIGS. 8–11, the shear deformation testing accessory 800 of the invention is illustrated. The shear deformation testing accessory 800 includes a generally C-shaped member 802 for receiving a shear deformation specimen tube generally designated by 804. A hand knurled knob specimen retaining assembly 805 is adjusted by the operator to hold the shear deformation specimen tube 804 in the support member 802. In FIG. 10, the specimen tube 804 includes an upper member 806 having an outwardly extending flange 807 and a lower ring member 808. The specimen tube lower member 808 is received within a base 810 of a separate ramming assembly used for loading the specimen tube 804 with the foundry sand to be tested. A plastic wiper ring 811 is carried by the base 810 for cleaning and alignment of the specimen tube 804. The shear deformation testing accessory 800 includes a pusher rod 812 received within the jaw support 104 carried by housing 106. The pusher rod 812 is threadedly received within a threaded flat stop member 814 that is initially spaced apart from the jaw support 104, as shown in FIG. 11. During the shear deformation testing, the pusher rod 812 moves toward the housing 106 and is stopped when the stop member 814 engages the jaw support 104. The pusher rod 814 engages the specimen tube lower member 808 causing the foundry sand sample contained within the specimen tube 804 to break at a plane or axis defined by the respective mating surface 806A and 808A of the upper and lower specimen tube members 806 and 808. The breaking or failure plane is labelled FAILURE PLANE in FIG. 11.

Referring to FIGS. 12–15, the cold shell tensile testing accessory 1200 of the invention is illustrated. The cold shell tensile testing accessory 1200 is used for cold shell tensile testing of a conventionally arranged "dog-bone" specimen 144A, as shown in FIG. 15. The cold shell tensile testing accessory 1200 includes a pusher bridge 1202, and a pair of removable tooling members 1204 and 1206 arranged for receiving the specimen 144A. The tooling members 1204 and 1206 and the specimen 144A are supported in a plane by a supporting member 1208. The tooling member 1204 is linked to the pusher bridge 1202 by a pivot pin 1210. The tooling member 1206 is mounted on a pivot pin 1212 which allows free pivotal movement or rotation of tooling members 1204 and 1206 and the pusher bridge 1202 about pin 1212 from right to left as shown. In accordance with a feature of the invention, a plurality of pads 1215 are mounted on the tooling members 1204 and 1206 and positioned to engage the specimen 144A and distribute the applied tensile load to the specimen. The pads 1215 are formed of a resilient material, such as rubber. The pads 1215 allow the specimen 144A to break along a central necked down portion and avoiding a shoulder break where the tooling members 1204 and 1206 would otherwise directly engage the specimen 144A without the pads 1215. The cold shell tensile testing accessory 1200 includes a pusher rod 1216 received within the jaw support 104 carried by housing 106. In FIG. 12, the direction of movement of arm 102 is indicated by an arrow labelled MACHINE MOVEMENT and the direction of the tensile load applied to the specimen 144A is indicated by an arrow labelled TENSILE LOAD.

Referring to FIGS. 16–19, the green sand tensile testing accessory 1600 of the invention is illustrated. The green sand tensile testing accessory 1600 includes a pair of members 802 for receiving a green sand tensile testing specimen tube generally designated by 1604. A hand knurled knob specimen retaining assembly 1605 is adjusted by the operator to hold the green sand tensile testing specimen tube 1604 on the support members 1602. Referring to FIGS. 17, 18 and 19, the green sand tensile testing specimen tube 1604 includes an upper and lower mating members 1606 and 1608 with the upper member 1606 formed with a flange 1610. The upper and lower members define a generally parabola shaped inner wall 1612, as shown in FIG. 18. When the green sand sample is loaded into the specimen tube 1604, opposing compacting forces are applied to the green sand sample, represented by a pair of arrows each labelled F in FIG. 19.

The green sand tensile testing accessory 1600 includes a pusher rod 1612 received within the jaw support 104 carried by housing 106. The pusher rod 1612 is threadedly received within a threaded flat stop member 1614 that is initially spaced apart from the jaw support 104. During the green sand tensile testing, the pusher rod 1612 moves toward the housing 106 and is stopped when the stop member 1614 engages the jaw support 104. The pusher rod 1612 is connected to an equaling bridge 1616 that equally divides the force exerted by the push rod 1612 into two equal forces that are transmitted to the specimen tube flange member 1610 by a pair of push rods 1615. The two equal forces are applied at two symmetrically located points on the flange 1610 causing the foundry sand sample contained within the specimen tube 1604 to break under tensile load at a plane or axis defined by the respective mating surface 1606A and 1608A of the upper and lower specimen tube members 1606 and 1608. The breaking or failure plane is labelled SAND FAILURE PLANE in FIG. 16.

While the present invention has been described with reference to the details of the embodiments of the invention shown in the drawing, these details are not intended to limit the scope of the invention as claimed in the appended claims.

What is claimed is:

1. A system for testing foundry sand comprising:
   sensor means for sensing strength and strain characteristics of said foundry sand responsive to an applied force to a sample of said foundry sand and for generating a strength representative signal and a strain representative signal;
   processor means coupled to said sensor means for processing said generated strength and strain representative signals; said processor means includes means for receiving a user calibration selection, and means responsive to said user calibration selection for receiving user selected calibration adjustments; and display means coupled to and operatively controlled by said processor means for displaying a stress-strain curve responsive to said generated strength and strain representative signals.

2. A system as recited in claim 1 wherein said processor means includes means for identifying a reference force indicator value.

3. A system as recited in claim 1 wherein said processor means includes means for identifying a reference strain indicator value.

4. A system as recited in claim 1 wherein said sensor means includes a load cell for generating said strength representative signal of said foundry sand responsive to an applied force to a sample of said foundry sand.

5. A system as recited in claim 1 wherein said sensor means includes a linear variable displacement transducer for generating said strain representative signal of said foundry sand responsive to an applied force to a sample of said foundry sand.

6. A system as recited in claim 1 further includes a housing; a moveable arm carried by said housing; an test accessory mounted on said moveable arm; said test accessory receiving a foundry sand sample.

7. A system as recited in claim 6 wherein said test accessory mounted on said moveable arm includes a shear deformation testing accessory, said shear deformation testing accessory including a member for receiving a shear deformation specimen tube, said shear deformation specimen tube containing a foundry sand sample; said shear deformation specimen tube including a first member and second member, and said shear deformation testing accessory including a push rod engaging one of said first and second specimen tube members for breaking said foundry sand sample at a plane defined by said first and second specimen tube members.

8. A system for testing foundry sand as recited in claim 6 wherein said test accessory mounted on said moveable arm includes a cold shell tensile testing accessory, said cold shell tensile testing accessory including a support member, a pair of removeable tooling members carried by said support member for receiving a specimen, and a plurality of pads mounted on said tooling members, said pads engaging said specimen and distributing applied tensile load to said specimen.

9. A system for testing foundry sand as recited in claim 8 wherein said pads are formed of a resilient material.

10. A system for testing foundry sand as recited in claim 6 wherein said test accessory mounted on said moveable arm includes a green sand tensile testing accessory, said green sand tensile testing accessory including a member for receiving a green sand tensile specimen tube, said green sand tensile specimen tube containing a green sand sample; said green sand tensile specimen tube including a first member and second member, and one of said first and second green sand tensile specimen tube member having an outwardly extending flange and said green sand tensile testing accessory including a pair of push rods engaging said flange members for breaking said green sand sample at a plane.

11. A system for testing foundry sand as recited in claim 6 wherein said green sand tensile specimen tube has a generally parabolic shaped inner wall.

12. A system as recited in claim 1 wherein said processor means includes means utilizing said stress-strain curve of said foundry sand for identifying a maximum stress value MAX SIGMA and for identifying a maximum strain value E MAX.

13. A system as recited in claim 12 wherein said processor means includes means utilizing said stress-strain curve of said foundry sand for calculating a first area under said stress-strain curve extending from zero to said identified maximum strain value E MAX, said first area represented by W1.

14. A system as recited in claim 1 wherein said processor means includes means utilizing said stress-strain curve of said foundry sand for calculating a second area under said stress-strain curve from said identified maximum strain value E MAX to a predetermined cutoff value E2 following said maximum strength value, said second area represented by W2.

15. A system as recited in claim 14 wherein said processor means includes means for receiving user selected test parameters, and wherein said user selected test parameters includes said predetermined cutoff value E2.

16. A system as recited in claim 14 wherein said processor means includes means utilizing said stress-strain curve of said foundry sand for identifying a maximum deformation value at said predetermined cutoff value E2.

17. A system as recited in claim 14 wherein said processor means includes means utilizing said stress-strain curve of said foundry sand for calculating a slope of a line between a first and a second user selected values E1 and E2 following said maximum strength value E MAX, said slope represented by E.

18. A system as recited in claim 14 wherein said processor means includes means utilizing said stress-strain curve of said foundry sand for identifying deformation from the beginning of the test to said second predetermined value E2.

19. A method for testing foundry sand using a computer test system including a processor device and a display comprising the steps of:

sensing strength and strain characteristics of said foundry sand responsive to an applied force to a sample of said foundry sand and generating a strength representative signal and a strain representative signal;

utilizing said processor device, processing said generated strength and strain representative signals and generating a stress-strain curve responsive to said strain representative signal and said strength representative signal of said foundry sand;

utilizing said processor device, and receiving user calibration adjustments; and utilizing said processor device for operatively controlling said display and displaying said generated stress-strain curve.

20. A method for testing foundry sand as recited in claim 19 further includes the steps of utilizing said generated stress-strain curve and calculating an area under said generated stress-strain curve from a starting test value to a maximum strength value E MAX of said generated stress-strain curve, said area represented by W1.

21. A method for testing foundry sand as recited in claim 20 further includes the steps of utilizing said stress-strain curve of said foundry sand, identifying a slope of a line between a first and a second user selected values following said maximum strength values E1 and E2, said slope represented by E.

22. A method for testing foundry sand as recited in claim 21 further includes the steps of utilizing said stress-strain curve of said foundry sand and identifying deformation from the beginning of the test to said second user selected value E2.

23. A method for testing foundry sand as recited in claim 22 further includes the steps of utilizing said stress-strain curve of said foundry sand and identifying a second area under said stress-strain curve from said identified maximum strength value E MAX to said second user selected value E2 following said maximum strength value, said second area represented by W2.

* * * * *